United States Patent
Schrank et al.

(10) Patent No.: US 9,570,390 B2
(45) Date of Patent: Feb. 14, 2017

(54) SEMICONDUCTOR DEVICE WITH INTEGRATED HOT PLATE AND RECESSED SUBSTRATE AND METHOD OF PRODUCTION

(71) Applicant: ams AG, Unterpremstaetten (AT)

(72) Inventors: Franz Schrank, Graz (AT); Martin Schrems, Eggersdorf (AT)

(73) Assignee: AMS AG, Unterpremstaetten (AT)

( * ) Notice: Subject to any disclaimer, the term of this patent is extended or adjusted under 35 U.S.C. 154(b) by 57 days.

(21) Appl. No.: 14/651,197

(22) PCT Filed: Dec. 5, 2013

(86) PCT No.: PCT/EP2013/075665
§ 371 (c)(1),
(2) Date: Jun. 10, 2015

(87) PCT Pub. No.: WO2014/090681
PCT Pub. Date: Jun. 19, 2014

(65) Prior Publication Data
US 2015/0303141 A1 Oct. 22, 2015

(30) Foreign Application Priority Data
Dec. 10, 2012 (EP) ..................................... 12196321

(51) Int. Cl.
*H01L 23/34* (2006.01)
*H01L 23/64* (2006.01)
(Continued)

(52) U.S. Cl.
CPC ........... *H01L 23/528* (2013.01); *G01N 27/128* (2013.01); *G01N 27/14* (2013.01);
(Continued)

(58) Field of Classification Search
CPC ................. H01L 23/345; H01L 23/647; H01L 2223/6672; H01L 31/024; H01L 31/270629
See application file for complete search history.

(56) References Cited

U.S. PATENT DOCUMENTS 6,110,825 A * 8/2000 Mastromatteo ... H01L 21/76898
257/E21.597
6,352,923 B1 * 3/2002 Hsuan ............... H01L 21/76898
257/E21.597
(Continued)

FOREIGN PATENT DOCUMENTS

WO 2002/050528 A1 6/2002
WO 2009/111874 A1 9/2009
(Continued)

*Primary Examiner* — David Zarneke
(74) *Attorney, Agent, or Firm* — McDermott Will & Emery LLP

(57) ABSTRACT

The semiconductor device comprises a substrate of semiconductor material, a dielectric layer on the substrate, an electrically conductive contact pad arranged in the dielectric layer, a hot plate arranged in the dielectric layer, a recess of the substrate at the location of the hot plate, and an integrated circuit, which operates the hot plate. An electrically conductive layer is arranged on a side of the substrate opposite the dielectric layer. The substrate is provided with a via hole above the contact pad, and an electrically conductive material connecting the electrically conductive layer with the contact pad is applied in the via hole. The recess and the via hole are formed in the same process step.

14 Claims, 6 Drawing Sheets

(51) Int. Cl.
  *H01L 31/024* (2014.01)
  *H01L 27/06* (2006.01)
  *H01L 23/528* (2006.01)
  *G01N 27/14* (2006.01)
  *H01L 23/522* (2006.01)
  *G01N 27/12* (2006.01)
  *G01N 33/00* (2006.01)

(52) U.S. Cl.
  CPC ....... *G01N 33/0004* (2013.01); *H01L 23/345* (2013.01); *H01L 23/5226* (2013.01); *G01N 33/0016* (2013.01); *H01L 23/647* (2013.01); *H01L 27/0629* (2013.01); *H01L 31/024* (2013.01); *H01L 2223/6672* (2013.01); *H01L 2924/0002* (2013.01)

(56) References Cited

U.S. PATENT DOCUMENTS

| | | |
|---|---|---|
| 7,495,300 B2 | 2/2009 | Gardner et al. |
| 8,686,555 B2 * | 4/2014 | Yaralioglu ............ H01L 23/345 257/704 |
| 9,018,688 B2 * | 4/2015 | Yamaguchi ......... H01L 27/1464 257/292 |
| 2008/0283951 A1 | 11/2008 | Nabe et al. |
| 2008/0290984 A1 * | 11/2008 | Wei ........................ H05K 1/167 338/309 |
| 2010/0073122 A1 * | 3/2010 | Le Neel ................ H01C 17/265 338/25 |
| 2013/0001765 A1 * | 1/2013 | Yaralioglu ............ H01L 23/345 257/704 |
| 2013/0033303 A1 * | 2/2013 | Morimoto ............. H01L 23/345 327/512 |
| 2013/0141834 A1 * | 6/2013 | Le Neel ................... H01G 7/04 361/301.1 |
| 2013/0264610 A1 * | 10/2013 | Chen ..................... B81C 1/0023 257/252 |
| 2014/0252538 A1 * | 9/2014 | Bao ..................... H01L 23/5256 257/529 |

FOREIGN PATENT DOCUMENTS

| | | |
|---|---|---|
| WO | 2010/006916 A1 | 1/2010 |
| WO | 20101081603 A1 | 7/2010 |
| WO | 20121114400 A1 | 8/2012 |

* cited by examiner

SEMICONDUCTOR DEVICE WITH INTEGRATED HOT PLATE AND RECESSED SUBSTRATE AND METHOD OF PRODUCTION

BACKGROUND OF THE INVENTION

WO 02/50528 A1 discloses a gas sensor system integrated on a single chip, including a microsensor with a microheater of essentially round, elliptic or polygonal structure and electronic circuits. The microsensor is arranged on a thermally isolated membrane.

U.S. Pat. No. 7,495,300 B2 discloses a gas-sensing semiconductor device on silicon, comprising a resistive heater made of tungsten embedded in a thin silicon oxide layer that is formed over a recess of the silicon substrate. The device can be monolithically integrated with a circuitry using a CMOS process.

WO 2010/006916 A1 discloses a semiconductor device with a through-silicon via. A connection pad is arranged in the insulation layer of an SOI substrate, and a contact hole is formed in the silicon above the pad. A metallization is applied to the pad and to the sidewall of the hole and connects the pad with a top metal.

SUMMARY OF THE INVENTION

The semiconductor device comprises a substrate of semiconductor material, a dielectric layer on the substrate, an electrically conductive contact pad arranged in the dielectric layer, a hot plate arranged in the dielectric layer, a recess of the substrate at the location of the hot plate, and an integrated circuit, which operates the hot plate. An electrically conductive layer is arranged on a side of the substrate opposite the dielectric layer. The substrate is provided with a via hole above the contact pad, and an electrically conductive material connecting the electrically conductive layer with the contact pad is applied in the via hole.

In an embodiment of the semiconductor device the contact pad is electrically connected with the integrated circuit.

In a further embodiment of the semiconductor device the recess is formed by a plurality of openings.

In further embodiments of the semiconductor device the openings are arranged above the area occupied by the hot plate, around the area occupied by the hot plate or both above and around the area occupied by the hot plate.

In a further embodiment of the semiconductor device the openings are cylindrical.

The method of producing a semiconductor device comprises the steps of applying a dielectric layer on a substrate of semiconductor material and arranging an electrically conductive contact pad and a hot plate in the dielectric layer, and forming a recess in the substrate at the location of the hot plate. The recess and a via hole penetrating the substrate and uncovering the contact pad are formed in the same process step, and an electrically conductive material is applied in the via hole in contact with the contact pad, thus forming a through-substrate via.

In a variant of the method the recess is made free from the electrically conductive material by not applying the electrically conductive material in the recess or by applying the electrically conductive material in the recess and subsequently removing it out of the recess.

In a further variant of the method tungsten is used as the electrically conductive material.

In a further variant of the method the recess is formed by a plurality of openings that are separately etched in the semiconductor material in the same process step.

In further variants of the method the openings are arranged above the area occupied by the hot plate, around the area occupied by the hot plate or both above and around the area occupied by the hot plate.

In a further variant of the method the openings are cylindrically formed.

The following is a detailed description of examples of the semiconductor device and the method of production in conjunction with the accompanying drawings.

DETAILED DESCRIPTION

Figure 1:
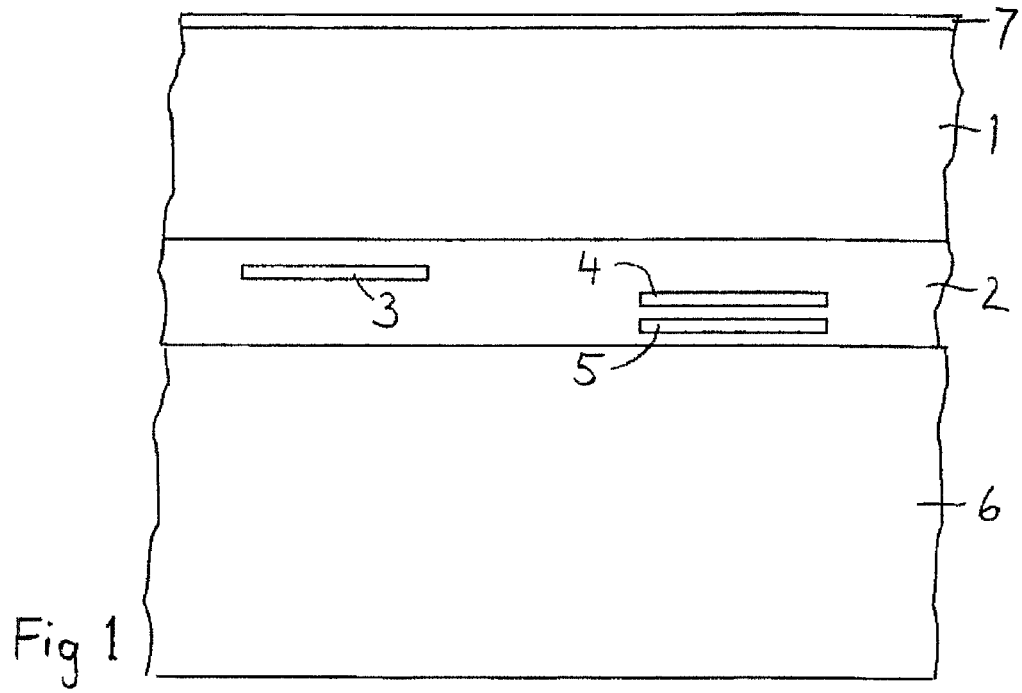
FIG. 1 shows a cross section of an arrangement of a semiconductor substrate on a handling wafer.

FIG. 1 shows a cross section of a semiconductor substrate 1 comprising a dielectric layer 2, in which a contact pad 3 and a hot plate 4 are embedded. The contact pad 3 is provided as an electric terminal and may be connected with conductor tracks or components of an integrated circuit. The hot plate 4 is provided to heat an element of the device, which may be a sensor, for instance. A sensor structure is indicated in FIG. 1 by a sensor layer 5 arranged at a small distance from the hot plate 4. The element that is to be heated may instead be arranged in direct contact with the hot plate 4. A sensor may comprise one, two or more individual layers.

The hot plate 4 can be produced by method steps that are available in a process that is applied to produce the integrated circuit, which may be a CMOS process, for example. The hot plate 4 may especially be produced in the same way as the contact pad 3 as part of a structured metal layer of a wiring or the like. The hot plate 4 can be a resistive heater comprising a material that can be heated by an electric current. Suitable materials are a metal like tungsten or a doped semiconductor material like polysilicon, for example. If the hot plate 4 is intended as a resistive heater, it is provided with electrical connections for the application of a voltage and may be formed as a conductor track. It may especially have a meandering shape to cover an area that is broader than the width of the conductor track.

The substrate 1 may be fastened to a handling wafer 6 to facilitate the handling during subsequent process steps. The handling wafer 6 is bonded to the dielectric layer 2. The substrate 1 may then be thinned if desired; the handling wafer 6 provides a sufficient mechanical stability of the arrangement. A coating 7 may be applied to the surface of the substrate 1 opposite the handling wafer 6.

Figure 2:
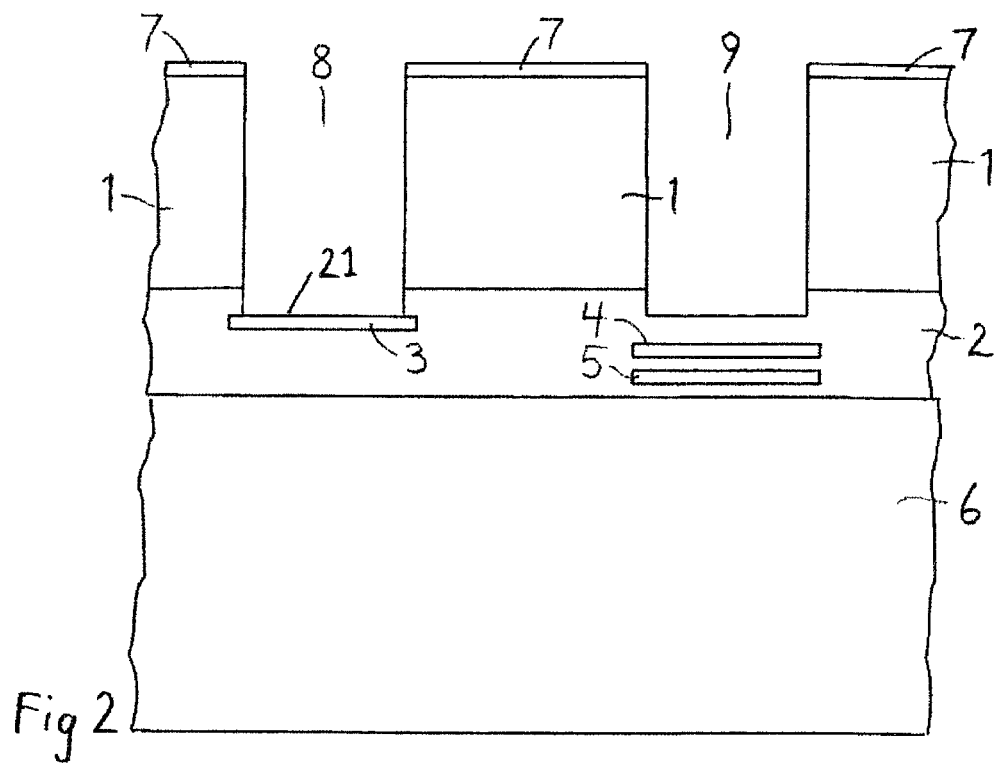
FIG. 2 shows a cross section according to FIG. 1 after the production of openings in the substrate.

FIG. 2 shows a cross section according to FIG. 1 after the formation of openings in the substrate 1, which include at least a via hole 8 and a recess 9. The openings can be produced by an etching step using a conventional mask technique. The etching is performed until the via hole 8 and the recess 9 completely penetrate the semiconductor material. The recess 9 is formed above the hot plate 4 in order to remove the semiconductor material from the vicinity of the hot plate 4. The semiconductor material has a high thermal conductivity and is liable to impair the operation of the hot plate 4 by absorbing the generated heat. A contact surface 21 of the contact pad 3 is uncovered by removing a portion of the dielectric layer 2 at the bottom of the via hole 8. The dielectric layer 2 can be removed by further etching, for example, in particular by using the same mask with a different etching agent. In this embodiment it is tolerated that a portion of the dielectric layer 2 is also removed at the bottom of the recess 9, which is thus lowered, as shown in FIG. 2.

Figure 3:
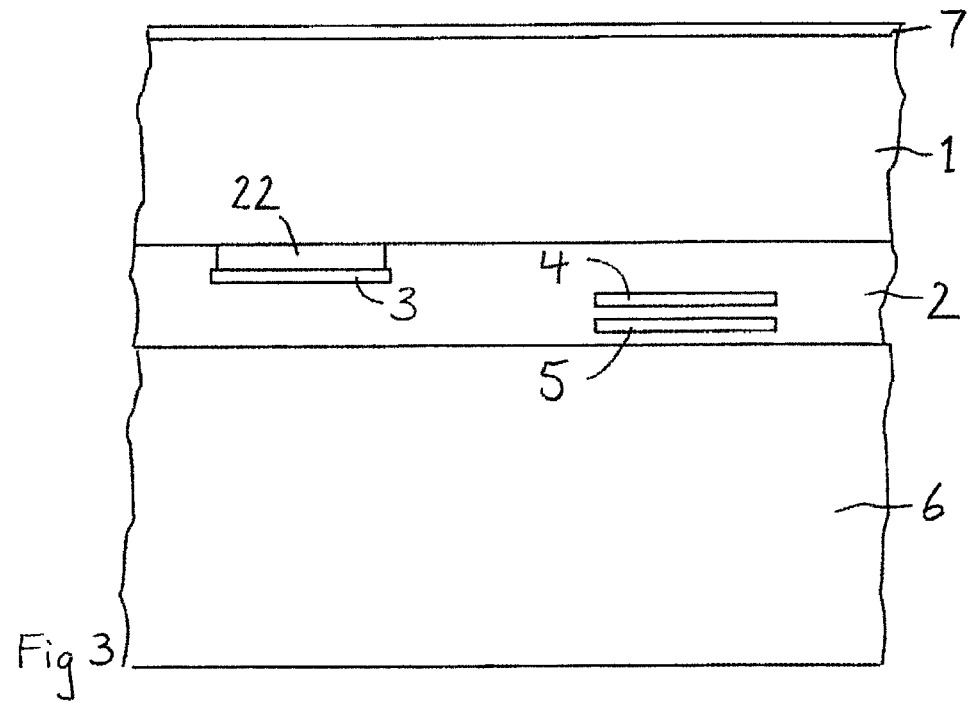
FIG. 3 shows a cross section of a further embodiment of the arrangement according to FIG. 1.

FIG. 3 shows a cross section of a further embodiment of the arrangement according to FIG. 1. In FIG. 3 the elements corresponding to similar elements of the embodiment according to FIG. 1 are designated with the same reference numerals. In the embodiment according to FIG. 3 a void 22 is formed between the contact pad 3 and the semiconductor substrate 1. An example of a method of producing this arrangement comprises the steps of applying the dielectric layer 2, in which the contact pad 3 and the hot plate 4 are embedded, on the handling wafer 6 and removing a portion of the dielectric layer 2 from the contact surface 21 the contact pad 3. Then the substrate 1 is bonded to the handling wafer 6 by means of the dielectric layer 2 as bonding layer. In this way the arrangement according to FIG. 3 is formed comprising the void 22 between the contact pad 3 and the semiconductor substrate 1.

Figure 4:
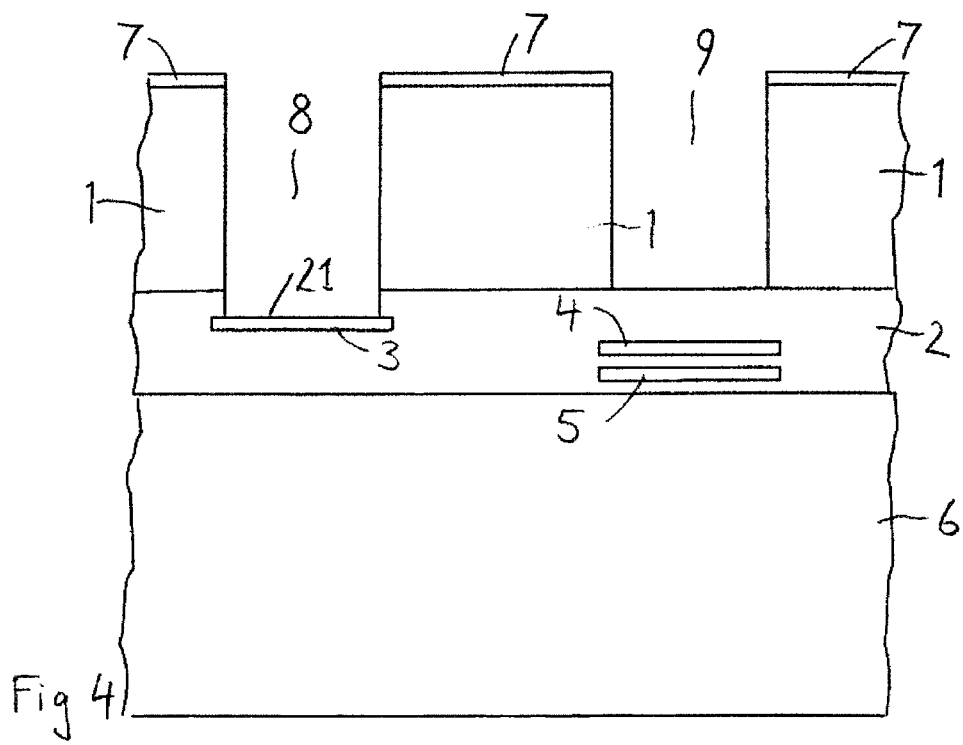
FIG. 4 shows a cross section according to FIG. 3 after the production of openings in the substrate.

FIG. 4 shows a cross section according to FIG. 2 after the formation of the via hole 8 and the recess 9. In FIG. 4 the elements corresponding to similar elements of the embodiment according to FIG. 2 are designated with the same reference numerals. Because of the void 22, the contact surface 21 of the contact pad 3 is already uncovered when the via hole 8 is completely etched through the substrate 1. A further etching step using a different etching agent to remove material of the dielectric layer 2 is therefore not necessary in this embodiment. The bottom of the recess 9 is not lowered but remains at the level of the plane of the boundary between the substrate 1 and the dielectric layer 2. The description of the following method steps equally applies to the embodiments according to FIGS. 1 and 3 and will be illustrated by further figures for the embodiment according to FIG. 1.

Figure 5:
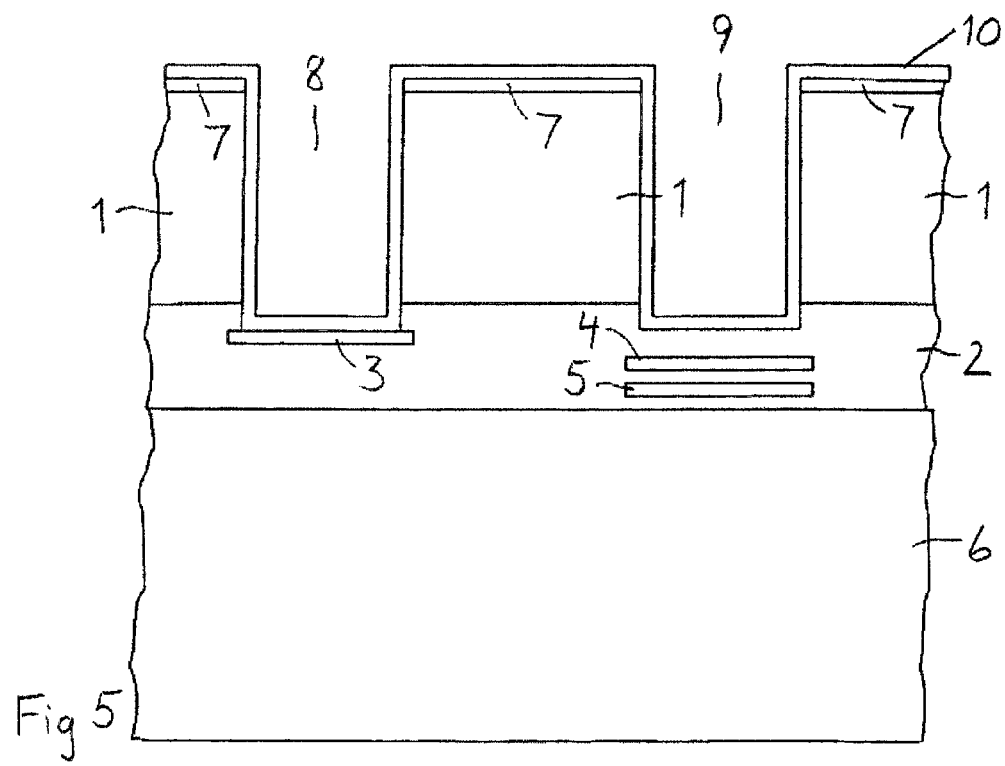
FIG. 5 shows a cross section according to FIG. 2 after the application of a dielectric material.
Figure 6:
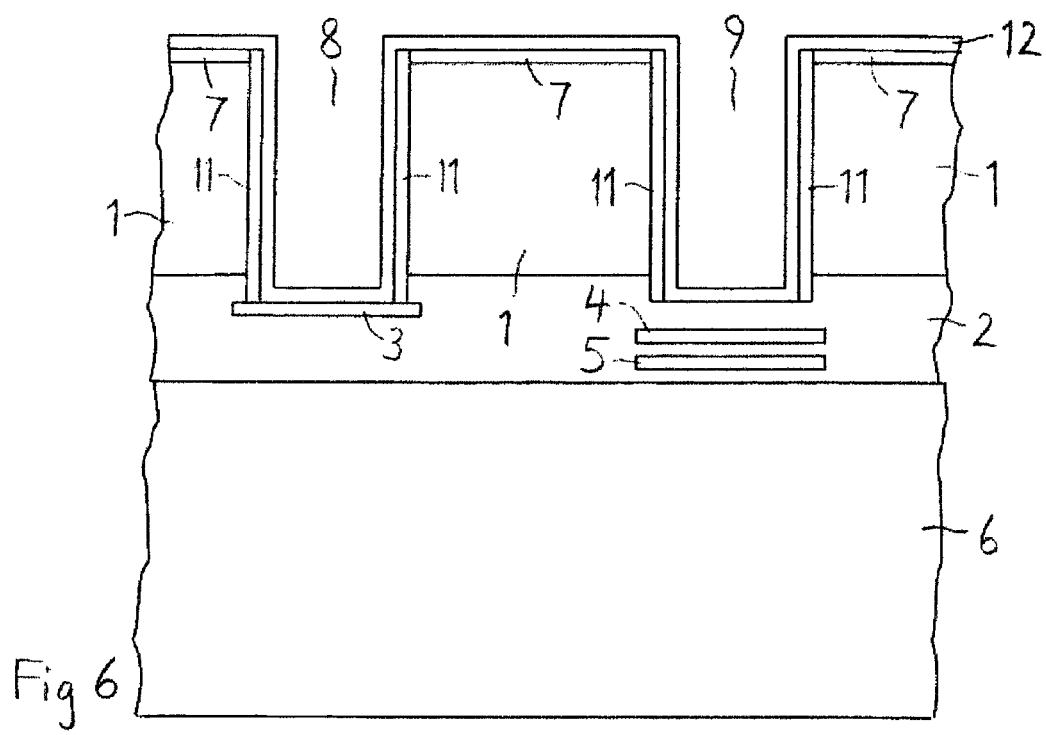
FIG. 6 shows a cross section according to FIG. 5 after the application of an electrically conductive material.

FIG. 5 shows a cross section according to FIG. 2 after an optional application of a layer of dielectric material 10, which may be an oxide of the semiconductor material, for example, in particular silicon dioxide. The dielectric material 10 or, instead, a thermal oxidation insulates the semiconductor material at the sidewall of the via hole 8. This insulation is appropriate but need not be provided in all embodiments. The dielectric material 10 is removed from the surface of the contact pad 3. This can be done by an anisotropic spacer etching technique, which also removes the dielectric material 10 from the upper surface of the substrate 1 outside the via hole 8 and leaves an insulating sidewall spacer 11 inside the via hole 8 as shown in FIG. 6. A similar spacer 11 is formed in the recess 9 above the hot plate 4, but the latter spacer 11 is not important for the function of the device.

FIG. 6 shows a cross section according to FIG. 5 after the application of a layer of an electrically conductive material 12, which contacts the contact pad 3 at the bottom of the via hole 8 and forms a through-substrate via as an electrically conductive interconnect.

Figure 7:
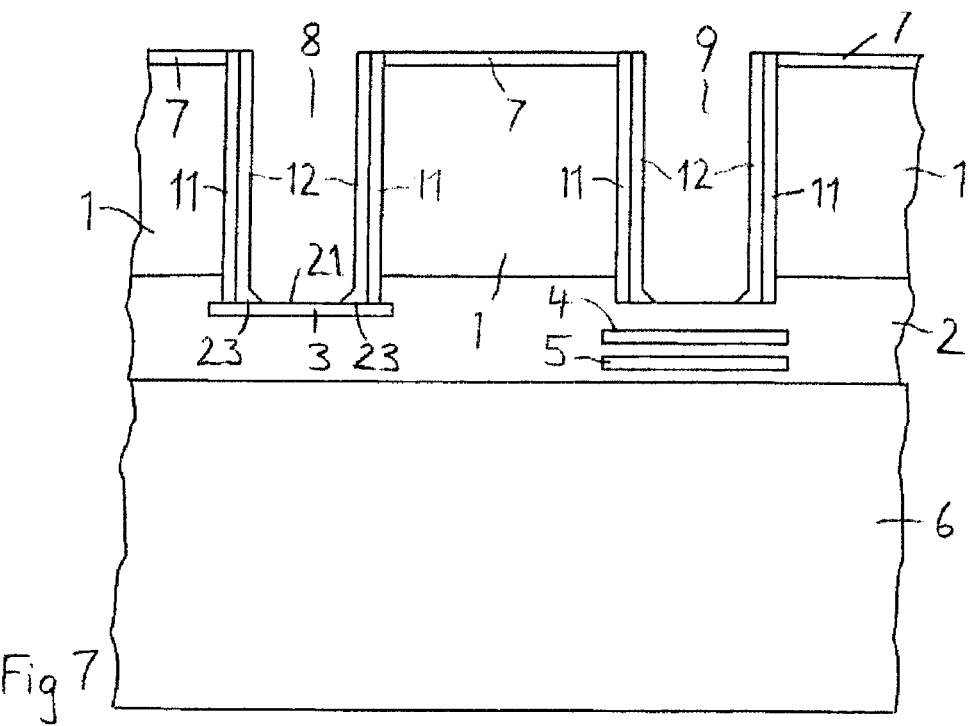
FIG. 7 shows a cross section according to FIG. 6 after a partial removal of the electrically conductive material.

FIG. 7 shows a cross section according to FIG. 6 after a partial removal of the electrically conductive material 12, in order to remove the electrically conductive material 12 from the upper surface of the substrate 1 outside the via hole 8. This can be done by an anisotropic spacer etching technique, which may also partially remove the electrically conductive material 12 from the bottom of the via hole 8. In this case only a marginal contact 23 is left between the contact surface 21 of the contact pad 3 and the electrically conductive material 12 remaining on the sidewall of the via hole 8. By an appropriate adjustment of the manufacturing process, it is instead possible to maintain at least a thin residual layer of the electrically conductive material 12 on the entire contact surface 21 of the contact pad 3, and this latter alternative is favorable. The portion of the electrically conductive material 12 that is left in the via hole 8 forms the electric conductor of the through-substrate via, as shown in FIG. 7. The portion of the electrically conductive material 12 that is left in the recess 9 above the hot plate 4 is removed if it is liable to impair the operation of the hot plate 4, particularly if it is a metal with a high thermal conductivity.

Figure 8:
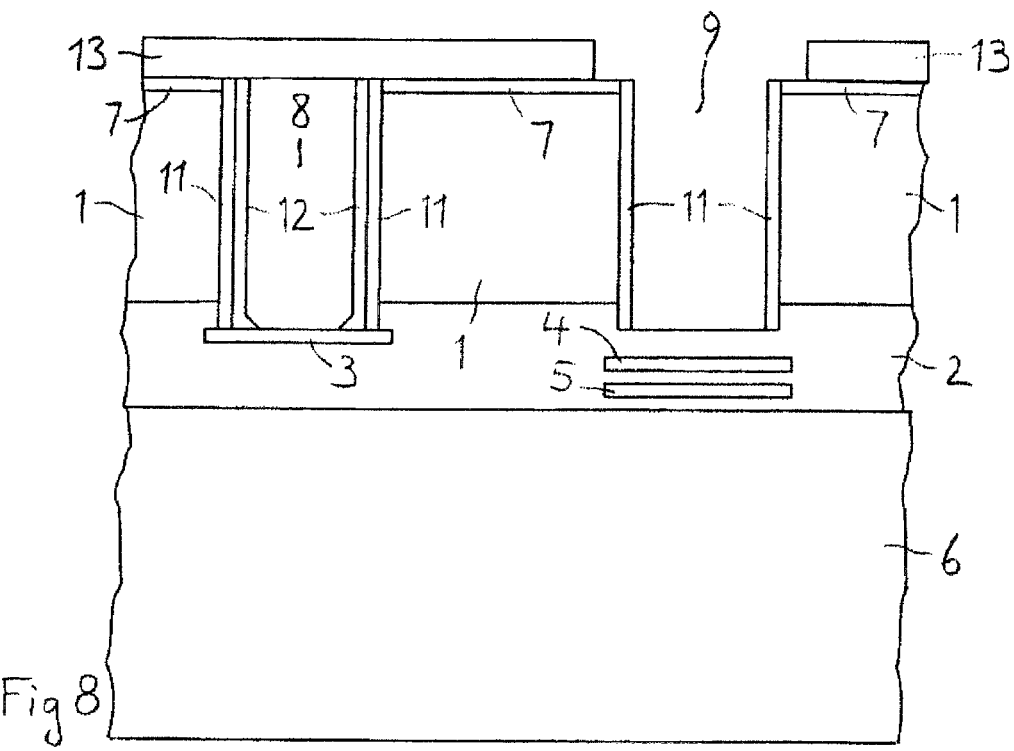
FIG. 8 shows a cross section according to FIG. 7 after a further partial removal of the electrically conductive material.

FIG. 8 shows a cross section according to FIG. 7 after the application of a mask 13 covering the via hole 8 and comprising an opening above the recess 9. The mask 13 can be formed as a thin film, for instance, using a dry-film process known per se, rendering a planar covering layer as shown in FIG. 8. Instead it is possible to fill the via hole 8 completely with the material of the mask or to cover the entire surface, including the inner surface of the via hole 8, with a thin mask layer by using a method like nano-coat spray coating, for instance. The mask 13 protects the through-substrate via when the electrically conductive material 12 is removed out of the recess 9, which can be effected by an etching step. This method step is not necessary if the electrically conductive material 12 is not applied as an entire layer but confined to the via hole 8, using a suitable mask to cover the recess 9. However, the described method is practically favorable, because a spatially selective deposition of electrically conductive material may involve some difficulty. FIG. 8 shows the recess 9 after the removal of the electrically conductive material 12.

Figure 9:
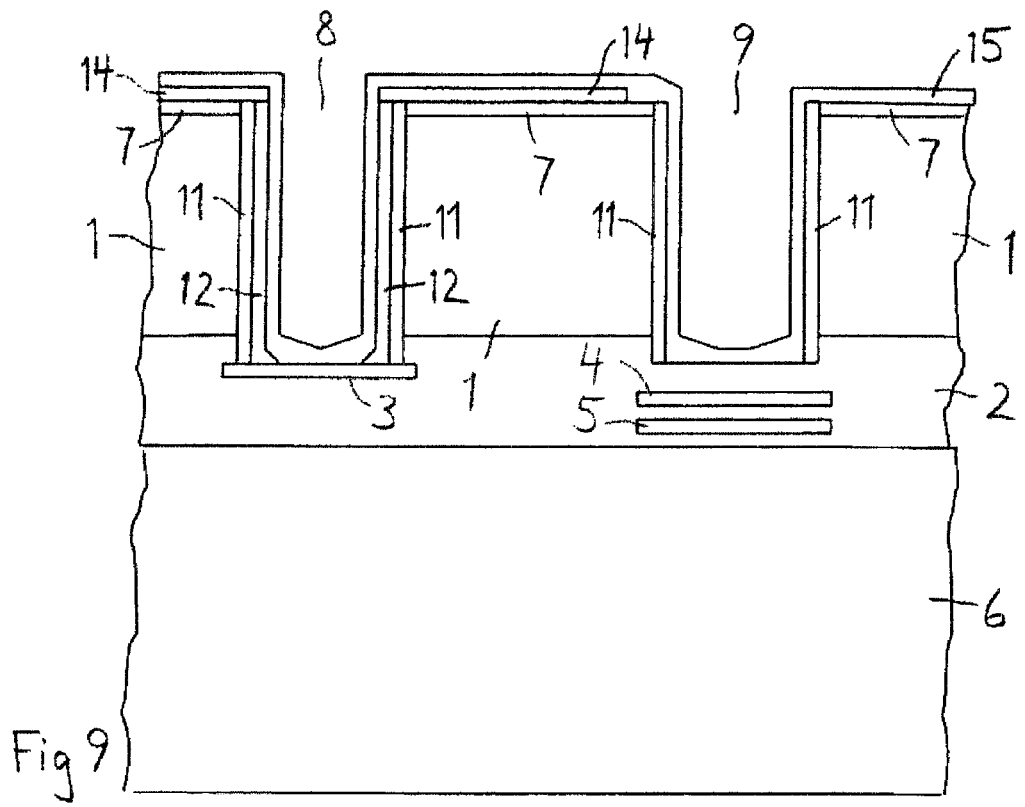
FIG. 9 shows a cross section according to FIG. 8 after the application of an electrically conductive layer and a passivation.

FIG. 9 shows a cross section according to FIG. 8 after the application of an electrically conductive layer 14 in contact with the electrically conductive material 12 remaining in the via hole 8, and a passivation 15. The electrically conductive layer 14 is provided on the upper surface as an electric connection of the through-substrate via. A bump contact or solder ball may be arranged on the electrically conductive layer 14 in an opening of the passivation 15 to form an external electric terminal.

Figure 10:
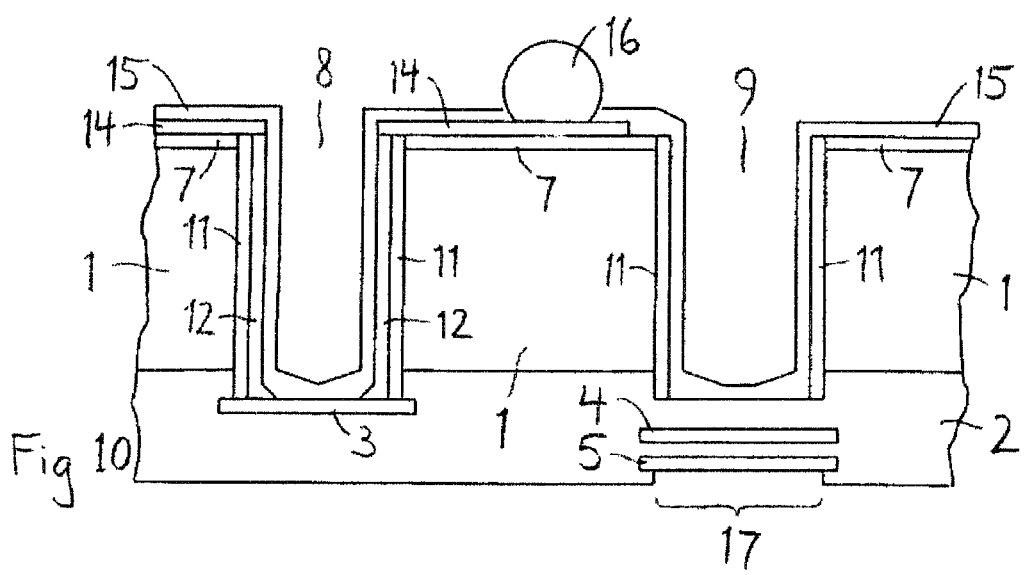
FIG. 10 shows a cross section according to FIG. 9 after the application of a solder ball and the removal of the handling wafer.

FIG. 10 shows a cross section according to FIG. 9 after the application of the solder ball 16 and the removal of the handling wafer 6. When the handling wafer 6 is removed, a window 17 for improved access to the sensor may optionally be formed in the dielectric layer 2. There are applications which do not require such a window. A direct access to the sensor is not necessary, for example, if the sensor layer 5 is capacitively coupled to the environment, and the gas that is to be detected changes the measured capacitance.

Figure 11:
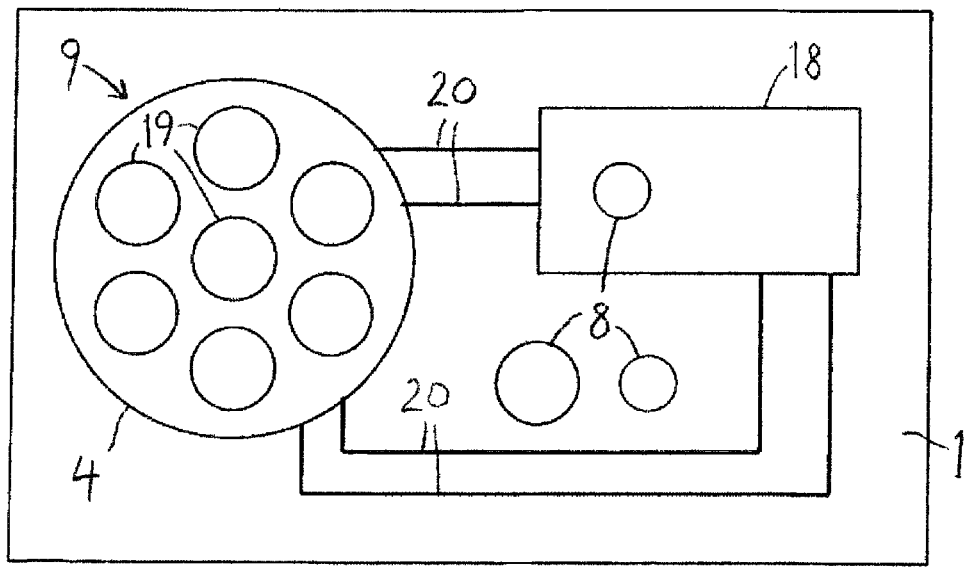
FIG. 11 shows a schematic plan view of an embodiment of the semiconductor device.

FIG. 11 shows a schematic plan view of an embodiment of the semiconductor device. An integrated circuit 18 is arranged in the substrate 1 as a read-out and control circuit. At least one through-substrate via is located in a via hole 8 of the substrate 1, and at least one integrated hot plate 4 is provided with a recess 9 in the substrate 1. The integrated circuit 18 is connected with the hot plate 4 and with the element that is to be heated by means of electrical connections 20, which may be provided for supplying the heating current and for performing a measurement or for detecting electric signals from the heated element, for example.

The embodiment according to FIG. 11 comprises three cylindrical via holes 8, but there can be any number of via holes 8 of any shape in the substrate 1. The via holes 8 can have the same diameter or different diameters as shown, and they can have the same or different shapes. The through-substrate vias can be used to connect terminals of the substrate 1, in particular terminals of the integrated circuit 18, with one another or with terminals of a further substrate or circuit board.

There can be any number of integrated hot plates 4 of any shape, whether equal or different. The recess 9 above the hot plate 4 may also have various shapes. The recess 9 may form a single opening, for example, especially an opening that continuously extends over the whole area of the hot plate 4. In the embodiment according to FIG. 11 the hot plate 4 is circular and the recess 9 is formed by a plurality of openings 19, which each have a cylindrical shape. The recess 9 may comprise any number of openings 19 of any shapes and dimensions, whether equal or different. In the example shown in FIG. 11 the openings 19 all have the same diameter, but the dimensions of the openings 19 may instead vary. If there are two or more hot plates 4, the shapes of the appertaining recesses 9 and eventually also the numbers of the openings 19 may differ. A recess 9 formed by several openings 19 has the advantage of rendering a greater mechanical stability of the device in comparison with a substrate that is recessed in the entire area of the hot plate 4. On the other hand the arrangement of the openings 19 can be sufficiently dense to provide an appropriate thermal isolation of the hot plate 4.

Figure 12:
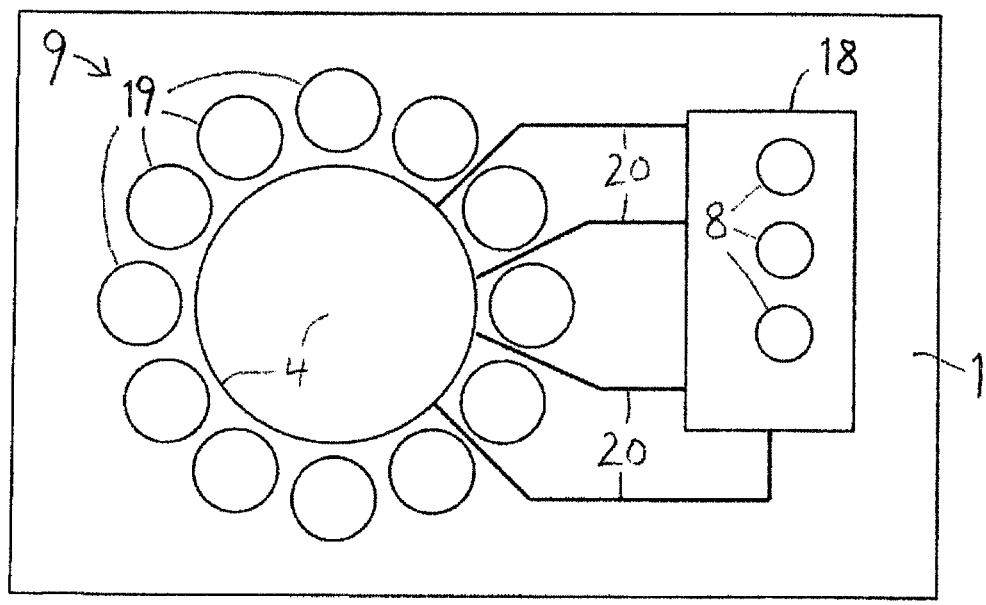
FIG. 12 shows a schematic plan view of a further embodiment of the semiconductor device.

FIG. 12 shows a schematic plan view of a further embodiment of the semiconductor device. An integrated circuit 18 is arranged in the substrate 1, which further comprises at least one through-substrate via located in a via hole 8 and at least one hot plate 4 provided with a recess 9 in the substrate 1. The integrated circuit 18 is connected with the hot plate 4 and with the element that is to be heated by means of electrical connections 20. The example shown in FIG. 12 comprises three cylindrical via holes 8 of the same diameter. The via holes 8 can have different diameters or different shapes, and there can be any number of via holes 8 in the substrate 1.

In the embodiment according to FIG. 12 the recess 9 is arranged at the location of the hot plate 4 outside the area of the hot plate 4 and is formed by a plurality of openings 19, which may each have a cylindrical shape, for instance. In the example shown in FIG. 11 the openings 19 have all the same diameter, but the dimensions of the openings 19 may instead vary. As in the previously described embodiment, the openings 19 may have different shapes and their number may vary. The openings 19 surround the area of the hot plate 4, so that the hot plate 4 is thermally isolated from the portion of the substrate 1 that is outside the area of the hot plate 4. A thermal isolation of the hot plate 4 from the bulk of the substrate 1 is thus provided while the hot plate 4 is still mechanically supported by a portion of the substrate 1 remaining inside the arrangement of the openings 19. Instead of a plurality of openings 19 only one annular opening may form the recess 9 around the hot plate 4. An annular recess 9 provides a better thermal isolation, but a plurality of spaced openings 19 provides a better mechanical stability.

Supplying a semiconductor device with an integrated hot plate and with advanced structures of electric interconnects is substantially facilitated with the simultaneous production of a through-substrate via and a recess for thermal isolation according to the above description.

The invention claimed is:

1. A semiconductor device, comprising:
   a substrate of semiconductor material;
   a dielectric layer on the substrate;
   an electrically conductive contact pad arranged in the dielectric layer;
   a hot plate arranged in the dielectric layer;
   a recess of the substrate at the location of the hot plate;
   an integrated circuit, which operates the hot plate;
   an electrically conductive layer being arranged on a side of the substrate opposite
   the dielectric layer;
   the substrate being provided with a via hole above the contact pad; and
   an electrically conductive material connecting the electrically conductive layer with the contact pad being applied in the via hole.

2. The semiconductor device according to claim 1, wherein the contact pad is electrically connected with the integrated circuit.

3. The semiconductor device according to claim 1, wherein the recess is formed by a plurality of openings.

4. The semiconductor device according to claim 3, wherein the openings are arranged above the area occupied by the hot plate.

5. The semiconductor device according to claim 3, wherein the openings are arranged around the area occupied by the hot plate.

6. The semiconductor device according to claim 3, wherein the openings are cylindrical.

7. A method of producing a semiconductor device, comprising:
   applying a dielectric layer on a substrate of semiconductor material and arranging an electrically conductive contact pad and a hot plate in the dielectric layer;
   forming a recess in the substrate at the location of the hot plate;
   the recess and a via hole penetrating the substrate and uncovering the contact pad being formed in the same process step; and
   an electrically conductive material being applied in the via hole in contact with the contact pad, thus forming a through-substrate via.

8. The method of claim 7, wherein
   the recess is made free from the electrically conductive material by not applying the electrically conductive material in the recess or by applying the electrically conductive material in the recess and subsequently removing it out of the recess.

9. The method of claim 7, wherein tungsten is used as the electrically conductive material.

10. The method of claim 7, wherein the recess is formed by a plurality of openings that are separately etched in the semiconductor material in the same process step.

11. The method according to claim 10, wherein the openings are arranged above the area occupied by the hot plate.

12. The method according to claim 10, wherein the openings are arranged around the area occupied by the hot plate.

13. The method according to claim 10, wherein the openings are cylindrically formed.

14. A semiconductor device, comprising:
a semiconductor substrate;
a through-substrate via in the semiconductor substrate;
an electrically conductive contact pad;
an electrically conductive layer, the through-substrate via electrically conductively connecting the electrically conductive layer with the contact pad;
a hot plate operated by an integrated circuit; and
a recess of the semiconductor substrate near the hot plate.

* * * * *